US00PP29925P3

(12) United States Plant Patent
Hansen

(10) Patent No.: US PP29,925 P3
(45) Date of Patent: Nov. 27, 2018

(54) **X *HEURECHELLA* PLANT NAMED 'PUMPKIN SPICE'**

(50) Latin Name: *X Heucherella (Heuchera x Tiarella)*
Varietal Denomination: Pumpkin Spice

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/530,532

(22) Filed: Jan. 25, 2017

(65) Prior Publication Data

US 2018/0213705 P1 Jul. 26, 2018

(51) Int. Cl.
*A01H 6/80* (2018.01)

(52) U.S. Cl.
USPC ..... Plt./441
CPC ..... *A01H 6/80* (2018.05)

(58) Field of Classification Search
USPC ..... Plt./441
See application file for complete search history.

*Primary Examiner* — Keith O. Robinson

(57) ABSTRACT

The new hybrid X *Heucherella* plant named 'Pumpkin Spice' with deeply-incised, palmately lobed foliage of variable coloration starting in the spring as bright orange with deep blood-red veins, transitioning to deep burgundy surrounding veins during flowering and burnt orange between the veins and in winter becoming deep green with black mahogany surrounding veins. The new plant begins flowering in late spring with a near white flowers on dark red stems. 'Pumpkin Spice' is suitable for landscaping en masse, as a specimen accent or as a container plant.

1 Drawing Sheet

Botanical denomination: X *Heucherella* (*Heuchera* x *Tiarella*);

Cultivar designation: 'Pumpkin Spice'.

BACKGROUND OF THE INVENTION

The present invention relates to a new and distinct intergeneric hybrid between coral bells and foam flower, both in the Saxifragaceae family and given the cultivar name of 'Pumpkin Spice' with the combined generic epithet X *Heucherella*. The intergeneric hybrid is sometimes given the common name of foamy bells. X *Heucherella* 'Pumpkin Spice' resulted from an intentional cross between a proprietary unreleased hybrid known as *Heuchera* K10-74-23 (not patented) as the female or seed parent and a proprietary unreleased seedling *Tiarella* 'Jade Peacock' U.S. Plant Pat. No. 26,730 as the male or pollen parent. The new plant was hybridized by the inventor at a wholesale perennial nursery in Zeeland, Mich., USA on Feb. 11, 2013. The new plant was selected from among many other crosses and X *Heucherella* seedlings growing at the same nursery which met the rigorous criteria of excellent foliage, vigor and habit established as breeding goals and was originally assigned the breeder code of 13-212-7. 'Pumpkin Spice' was selected from among many other crosses and X *Heucherella* seedlings growing at the same nursery in Zeeland, Mich. which met the rigorous criteria of excellent foliage, flower and habit established as breeding goals. X *Heucherella* 'Pumpkin Spice' has been asexually propagated since 2014 by basal cuttings at a nursery in Zeeland, Mich. and also by careful shoot-tip tissue culture propagation. The resultant asexually propagated plants have remained stable and exhibit the same characteristics as the original plant.

No plants of X *Heucherella* 'Pumpkin Spice' have been sold, under this or any name, in this country or anywhere in the world, prior to the filing of this application, nor has any disclosure of the new plant been made prior to the filing of this application with the exception of that which may have been disclosed or sold within one year of the filing of this application and was either derived directly or indirectly from the inventor.

BRIEF SUMMARY OF THE INVENTION

'Pumpkin Spice' differs from its parents as well as all other *Tiarella, Heuchera* or X *Heucherella* known to the applicant. Compared with the female parent, the new plant has creamy-colored flowers, the foliage more deeply dissected with longer lobes, and the foliage color is more bronze-red before flowering. Compared to the male parent, the new plant has more bronze-red foliage earlier in the spring with less rounded lobes, the flowers are more creamy-colored and the scapes are taller. The most similar cultivars include: X *Heucherella* 'Honey Rose' U.S. Plant Pat. No. 25,686, 'Redstone Falls' U.S. Plant Pat. No. 22,394 and 'Sweet Tea' U.S. Plant Pat. No. 21,296. All of the above have comparatively flat leaf blades. 'Honey Rose' has more reddish colored foliage with silver overlay, and the lobes are less dissected. 'Redstone Falls' is a more running habit, more reddish-colored foliage with slight silver overlay, and the leaf blades are not as long or sharply dissected as the new plant. 'Sweet Tea' has foliage that is more reddish colored, with less overlapping basal lobes.

The new plant differs from all *Heuchera*, X *Heucherella* and *Tiarella* known to the inventor in the following combined traits:

1. The foliage color is variable with the seasons and development of the leaves.
2. Leaves emerge in the spring with a bright orange with deep blood-red surrounding the veins.

3. Leaves transition to deep burgundy surrounding the veins and burnt orange contrast between the veins.
4. Leaves develop to a deep green with a deep black-mahogany surrounding the veins.
5. The flowers open near-white on dark red stems.
6. Foliage is deeply-incised the basal lobes frequently overlapping and protruding above the blade plane.
7. Habit is vigorous and mounded with multiple tightly clustered shoots emerging at the base all season.
8. The plant is robust, seedless, compact and is more heat and sun tolerant than typical X *Heucherella.*

BRIEF DESCRIPTION OF THE DRAWINGS

The photographs of the new plant demonstrate the overall appearance of the new plant including the unique traits. The plant in the photograph is of two-year-old plants at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
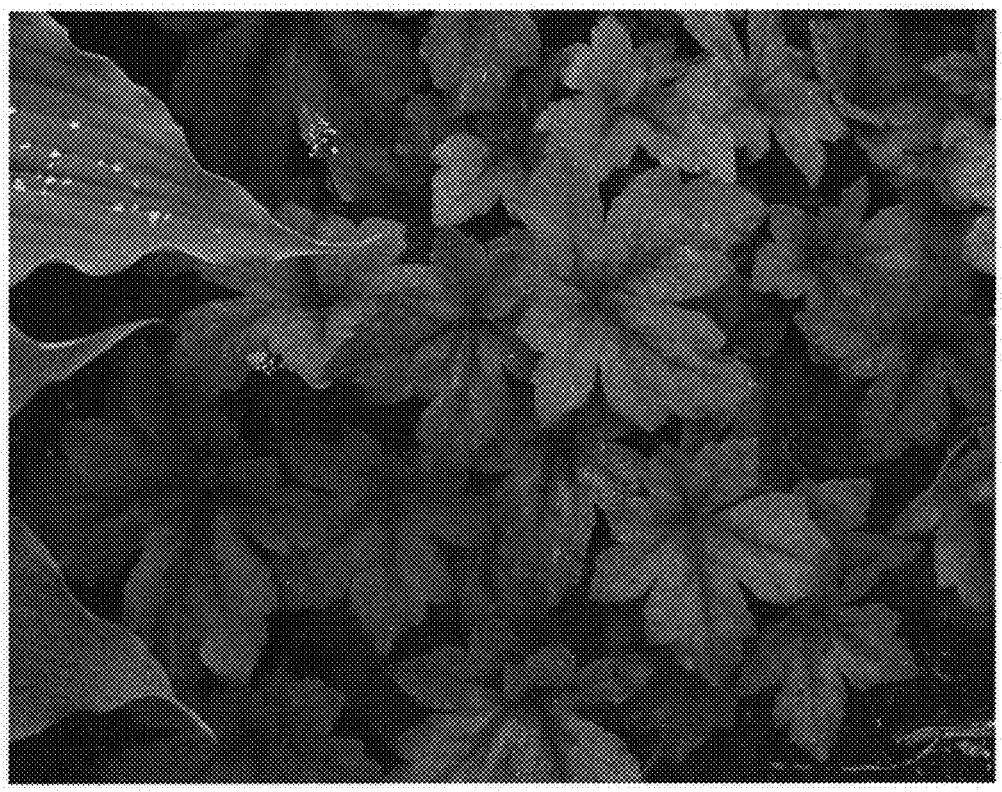
FIG. 1 shows a plant in a shaded outdoor trial garden in Zeeland, Mich. in early spring.
Figure 2:
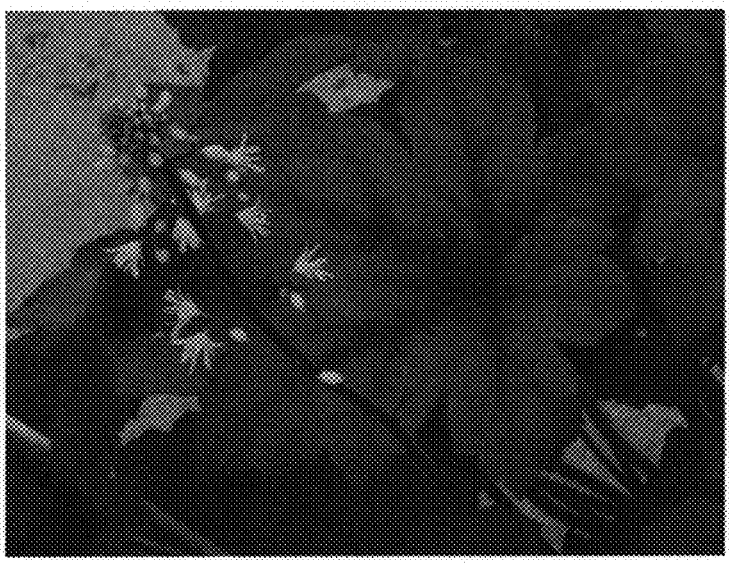
FIG. 2 shows a close-up of the foliage and flower panicle in mid-flowering season coloration in a greenhouse.

The following description is based on two-year-old plants growing in double poly greenhouse at a wholesale perennial nursery in Zeeland, Mich., USA. The new plant has not been grown under all possible environments and may phenotypically appear different under different conditions such as light, temperatures, fertilizer, and water, without any difference in genotype. The color descriptions are from the 2001 edition of The Royal Horticultural Society Colour Chart except where common dictionary terms are used.

Parentage: The female or seed parent, *Heuchera* K10-74-23, consists of genes from 'Southern Comfort' U.S. Plant Pat. No. 20,364, 'Pinot Gris' U.S. Plant Pat. No. 19,592 and 'Encore' U.S. Plant Pat. No. 19,578; the male or pollen parent was *Tiarella* 'Jade Peacock';

Plant habit: Hardy herbaceous perennial of tightly compact shoots with basal rosette of mounded foliage; foliage about 30 cm tall and about 50 cm in diameter;

Roots: Fibrous, finely branched; when actively growing near white RHS 155D to RHS 161D in color depending on soil type;

Growth rate: Rapid, rooting from cutting in 2 weeks and finishing in three-liter container in about 3 months; beginning to flower in 6 to 8 weeks following a 9 week vernalization;

Foliage: Palmately, irregularly, medium to deeply pentalobed; leaf blade pubescent adaxial and abaxial; apical lobes incised typically to nearly four-fifths of the way to petiole; medium to strongly lustrous abaxial and adaxial when expanding, matte surface above and slightly lustrous below when mature; broadly acute lobe apices with apices and margin micro-ciliate, and cordate base with lower lobes imbricate to about 3.5 cm and frequently folded in such a way that the basal lobes protrude above the plane of the leaf blade; blade to about 15.5 cm long and 15.5 cm wide, average about 12.0 cm long and 12.0 cm wide; center lobe sometimes irregularly fused from two lobes apical lobes or divided in middle;

Foliage color: Leaf blade color is seasonally variable; young expanding leaves adaxial nearest RHS N170B with center inner palm surrounding the base of veins nearest RHS 185A, young expanding abaxial between RHS 173B and RHS N172D; prior to flowering adaxial area surrounding veins nearest RHS 178A with area between veins between RHS 169B and RHS N172A, prior to flowering abaxial nearest RHS 179B; at flowering and mid-season adaxial nearest RHS 183A surrounding veins and a blend between RHS 166B and RHS N170A between veins, at flowering and mid-season abaxial between RHS 182B and RHS 183D; winter leaves adaxial area surrounding major veins nearest RHS N187A and distal portion and area between veins between RHS 137B and RHS 137C, winter leaves abaxial nearest RHS 178A with undertones of nearest RHS 146B;

Leaf margin: Ciliate and denticulate;

Leaf apex: Rounded with spicule or minutely cuspidate;

Leaf base: Cordate with imbricate basal lobes;

Leaf surface: Pubescent adaxial and abaxial;

Leaf quantity: Dense, about ten per division and 100 per plant;

Veins: Palmate; costate abaxial; puberulent adaxial and puberulent abaxial;

Vein color: Variable with season; adaxial expanding foliage nearest RHS 160A and abaxial nearest RHS N170C; at time of flowering and mid-season adaxial nearest RHS 182B, at time of flowering and mid-season abaxial main veins nearest RHS 182B; winter adaxial veins nearest RHS 146C and overwintered abaxial nearest RHS 147C with undertones of nearest RHS 178A;

Petiole: Terete, pubescent, base clasping; to about 20.0 cm long and about 3.5 mm diameter at base; average about 16.0 cm long and 3.2 mm diameter at base; wiry but flexible;

Petiole color: On emerging foliage nearest RHS 182B with thin dark stripe running down adaxial center nearest RHS 182A; at flowering and mid-season nearest RHS 185A on with thin adaxial strip of nearest RHS 183A; winter nearest RHS 187B;

Inflorescence: In branched panicle, about 10 panicles per plant; about 120 flowers per panicle; first panicle flowering about the end of May in Michigan and continuing for four weeks; individual panicles remaining in flower for about three weeks; individual flowers open for about four days; flower attitude mostly outwards;

Fragrance: None detected;

Peduncle: Terete, erect; puberulent; to about 50.0 cm tall and about 4.0 mm diameter at base; flowering portion about 25.0 cm long and about 4.5 cm across, medium density;

Peduncle attitude: Upright erect;

Peduncle branches: About thirty branches per panicle with two to five flowers per branch; extending between 15 to 30 degrees above horizontal; branches to about 1.5 cm long and about 0.7 mm diameter at base;

Peduncle color: Distal portion above foliage nearest RHS 187B, basal portion nearest RHS 183C;

Pedicel: Terete; puberulent; average about 2.5 mm long and 0.5 mm diameter at base;

Pedicel color: Nearest RHS 187A;

Buds one day prior to opening: Ellipsoid with rounded apex and rounded base; glandular to pubescent; about 3.0 mm long and 2.0 mm diameter;

Bud color: Nearest RHS N155B;

Flower: Perfect, campanulate, actinomorphic; about 6.0 mm deep and 7.5 mm in diameter at face; individual flowers lasting about three to four days on plant or as cut panicles;

Flower attitude: Mostly outwardly;

Calyx: Typically five sepals; glandular abaxial, glabrous adaxial; apex acute, fused at base into hypanthium; margin entire; sepals about 4.5 mm long and about 1.5 mm wide at point of fusion;

Calyx color: Abaxial lighter than RHS 155D; adaxial lighter than RHS 155D;

Petals: Five; adnate to calyx; spatulate, acute apex, attenuate base; margin entire; glabrous abaxial and adaxial; about 4.0 mm long and 0.8 mm wide at widest point;

Petal color: Abaxial and adaxial lighter than RHS N155B;

Androecium:

*Filaments*.—Typically five, thin, about 2.5 mm long and less than 0.5 mm in diameter; color white, lighter than RHS N155D.

*Anthers*.—Vestigial; basifixed; oblong to about 0.3 mm long and about 0.2 mm wide; color nearest RHS 155D.

*Pollen*.—Not observed.

Gynoecium:

*Pistil*.—One central two-beaked pistil.

*Style*.—About 5.0 mm long and 0.2 mm at apex flaring to 2.0 mm at base; color apex white, lighter than RHS 155D and base nearest RHS 145D.

*Stigma*.—Minute, about 0.2 mm diameter; color white, lighter than RHS 155D.

*Ovary*.—Two carpels; ovoid, apex tapering to meet style; rounded base and sides; about 2.0 mm across at base and 2.5 mm tall; color nearest RHS 155D.

Fruit and seed: Sterile; not observed;

Preferred cultural conditions: X *Heucherella* 'Pumpkin Spice' grows best with ample moisture and good drainage in part shade or protection from sun in the hottest part of the day. Cold hardy from USDA zones 4 to 9. X *Heucherella* 'Pumpkin Spice' is able to tolerate heat and humidity better than typical X *Heucherella*.

Disease and pest tolerance: Other pest and disease resistance and tolerance outside of that normal for X *Heucherella* is not known. Black vine weevil, *Otiorhynchus sulcatus*, have been found problematic on X *Heucherella*, but populations of this pest have not been observed in either the greenhouses or trial gardens where the new plant has been grown. Rust disease, *Puccinia heucherae*, although typical on some *Heuchera* cultivars, has not been observed on the new plant.

It is claimed:

1. The new and distinct ornamental plant named X *Heucherella* 'Pumpkin Spice' as herein described and illustrated.

* * * * *